United States Patent
Schneider et al.

(10) Patent No.: US 8,957,244 B2
(45) Date of Patent: Feb. 17, 2015

(54) PROCESS FOR PREPARING METHYL FORMATE BY REACTION OF METHANOL WITH CARBON MONOXIDE IN THE PRESENCE OF A CATALYST SYSTEM COMPRISING ALKALI METAL FORMATE AND ALKALI METAL ALKOXIDE

(71) Applicant: BASF SE, Ludwigshafen (DE)

(72) Inventors: Daniel Schneider, Manheim (DE); Klaus-Dieter Mohl, Hockenheim (DE); Martin Schäfer, Grünstadt (DE); Jürgen Paschold, Hochspeyer (DE); Joaquim Henrique Teles, Waldsee (DE); Stefan Rittinger, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/088,874

(22) Filed: Nov. 25, 2013

(65) Prior Publication Data
US 2014/0148614 A1    May 29, 2014

Related U.S. Application Data

(60) Provisional application No. 61/729,640, filed on Nov. 26, 2012.

(51) Int. Cl.
*C07C 67/36* (2006.01)
(52) U.S. Cl.
CPC ..................... *C07C 67/36* (2013.01)
USPC ....................................... 560/232
(58) Field of Classification Search
USPC ....................................... 560/232
See application file for complete search history.

(56) References Cited

U.S. PATENT DOCUMENTS

| | | | |
|---|---|---|---|
| 6,921,833 B1 | 7/2005 | Auer et al. | |
| 7,053,239 B2 * | 5/2006 | Adami et al. | 560/232 |
| 2004/0171704 A1 | 9/2004 | Fujimoto et al. | |
| 2005/0143598 A1 | 6/2005 | Adami et al. | |

FOREIGN PATENT DOCUMENTS

| | | |
|---|---|---|
| EP | 0596483 A2 | 5/1994 |
| WO | WO-0107392 A1 | 2/2001 |
| WO | WO-03089398 A1 | 10/2003 |

OTHER PUBLICATIONS

U.S. Appl. No. 13/721,296, filed Dec. 20, 2012, Schneider et al.
U.S. Appl. No. 13/721,392, filed Dec. 20, 2012, Bassler et al.
Arpe, Hans-Jürgen, Ullmann's Encyclopedia, "Industrielle Organische Chemie".
Reutemann, Werner, et al., "Formic Acid", Ullmann's Encyclopedia, (2005).
Process Economics Program, Formic Acid Derivatives, (1983).
Lim, Noni Suk-Chin, "Formic Acid by Kemira Process", PEP Review Dec. 2004.
Henkel, Klaus-Dieter, "Reactor Types and Their Industrial Applications", Ullmann's Encyclopedia of Industrial Chemistry, (2012).

* cited by examiner

*Primary Examiner* — Yong Chu
*Assistant Examiner* — Sonya Wright
(74) *Attorney, Agent, or Firm* — Drinker Biddle & Reath LLP (57) ABSTRACT

Process for preparing methyl formate by carbonylation of methanol by means of carbon monoxide in a carbonylation reactor in the presence of a catalyst system comprising alkali metal formate and alkali metal alkoxide to give a reaction mixture ($R_M$) which comprises methyl formate, alkali metal formate, alkali metal alkoxide and possibly unreacted methanol and unreacted carbon monoxide and is taken from the carbonylation reactor, wherein the reaction mixture ($R_M$) comprises at least 0.5% by weight of alkali metal alkoxide based on the total weight of the reaction mixture ($R_M$) and the molar ratio of alkali metal formate to alkali metal alkoxide in the reaction mixture ($R_M$) is greater than 1.

17 Claims, 1 Drawing Sheet

PROCESS FOR PREPARING METHYL FORMATE BY REACTION OF METHANOL WITH CARBON MONOXIDE IN THE PRESENCE OF A CATALYST SYSTEM COMPRISING ALKALI METAL FORMATE AND ALKALI METAL ALKOXIDE

CROSS-REFERENCE TO RELATED APPLICATIONS

This patent application claims the benefit of U.S. provisional patent application Ser. No. 61/729,640 filed on Nov. 26, 2012, incorporated in its entirety herein by reference.

The present invention relates to a process for preparing methyl formate by reaction of methanol with carbon monoxide in the presence of a catalyst system comprising an alkali metal formate and an alkali metal alkoxide.

Methyl formate (the methyl ester of formic acid) is an important intermediate for the preparation of formic acid, where methyl formate is hydrolyzed by means of water to form formic acid and methanol. Methyl formate is also used for preparing acetaldehyde by hydroisomerization over rhodium or iridium catalysts. In addition, the isomerization of methyl formate to acetic acid and the oxidative reaction of methyl formate with methanol over selenium catalysts to form dimethyl carbonate have been described (Hans-Jürgen Arpe, Industrielle Organische Chemie, 6$^{th}$ edition, 2007, page 48).

Methyl formate has been produced industrially for over 80 years by carbonylation of methanol. The carbonylation is generally carried out in the presence of a base as catalyst, in particular using sodium methoxide (sodium methylate) as catalyst. The reaction is generally carried out at about 70° C. and a pressure of up to 200 bar (Ullmanns Encyclopedia of Technical Chemistry, 6$^{th}$ edition (2003), volume 15, pages 5 to 8; Wiley-VCH-Verlag, DOI: 10.1002/14356007.a12_013).

The carbonylation of methanol is a homogeneously catalyzed equilibrium reaction in which the equilibrium is shifted in the direction of methyl formate with increasing carbon monoxide partial pressure and decreasing temperature. In the continuous carbonylation of methanol, not only the position of the equilibrium but also a sufficiently high reaction rate are necessary for an economic process with an acceptable space-time yield (STY). The reaction rate of the carbonylation of methanol can be increased by increasing the temperature or increasing the carbon monoxide partial pressure. However, increasing the reaction rate by the above-described methods is associated with disadvantages. Thus, increasing the temperature leads, as described above, to a deterioration in the position of the equilibrium, which in turn leads to a deterioration in the space-time yield. There are now numerous processes with various embodiments which are carried out to achieve an acceptable space-time yield under high pressure (up to 200 bar).

However, these high-pressure processes require specially designed reactors which are associated with high capital costs for the reactor.

WO 2001/07392 describes a process for the preparation of methyl formate, in which the reaction of methanol with carbon monoxide is carried out at a carbon monoxide pressure of from 9 to 18 MPa (from 90 to 180 bar) in the presence of from 0.05 to 0.5% by weight of an alkali metal methoxide, based on the weight of the liquid reactor feed. In the description of WO 2001/07392, it is indicated that the alkali metal methoxide used as catalyst is converted into the catalytically inactive alkali metal formate by, in particular, two undesirable but unavoidable secondary reactions. The alkali metal formate is also referred to as consumed catalyst or catalyst degradation product. The alkali metal formate can be formed here by reaction of alkali metal methoxide with methyl formate to give alkali metal formate and dimethyl ether according to equation (i). In addition, alkali metal formate is formed in the presence of traces of water from alkali metal methoxide and methyl formate by hydrolysis according to equation (ii), forming methanol and alkali metal formate. The secondary reactions (i) and (ii) are illustrated below for the example of the formation of sodium formate from sodium methoxide.

$$NaOCH_3 + HCOOCH_3 \rightarrow HCOONa + CH_3OCH_3 \quad (i)$$

$$NaOCH_3 + H_2O + HCOOCH_3 \rightarrow HCOONa + 2CH_3OH \quad (ii)$$

In the process according to WO 2001/07392, the methyl formate formed is driven off from the reactor output in a distillation apparatus. The unconsumed alkali metal methoxide used as catalyst can be recirculated to the carbonylation reactor. However, it is necessary to remove the catalyst degradation products in a desalting apparatus before recirculation in order to prevent precipitation of salts. The alkali metal formate occurring as catalyst degradation product can lead to deposits in the apparatuses and pipes through to blockage of pipes and valves because of its insufficient solubility. According to the teaching of WO 2001/07392, the content of alkali metal formate at the reactor outlet is preferably in the range from 0.1 to 0.3% by weight.

WO 2003/089398 likewise describes a process for preparing methyl formate from methanol and carbon monoxide in the presence of an alkali metal alkoxide in concentrations of from 0.01 to 2 mol per kg of liquid reaction mixture. There too, the alkali metal formate is described as undesirable catalyst degradation product which is discharged to prevent salt-like deposits. In addition, this process requires recirculation, which is complicated in terms of apparatus, of a gas stream which has an average superficial gas velocity in the range from 1 to 20 m/s.

Ullmanns Encyclopedia of Technical Chemistry (2005, chapter "Formic Acid", pages 6 to 7; Wiley-VCH-Verlag, DOI: 10.1002114356007.a12_013) also states that dimethyl ether and the catalytically inactive sodium formate are formed from sodium methoxide in an undesirable secondary reaction with methyl formate.

PEP-Review (Process Economics Program "Formic Acid", 1983, pages 50 to 52) describes a process for preparing methyl formate from methanol and carbon monoxide in the presence of sodium formate. The alkali metal formate formed is referred to as consumed or inactive catalyst. The catalyst, sodium. methoxide, can be recirculated to the reactor. However, for this it is necessary to discharge the sodium formate formed from the process in such amounts that the molar ratio of consumed catalyst (sodium formate) to catalyst (sodium methoxide) is not more than equimolar.

US 2004/0171704 describes a process for preparing methanol or formic esters by reaction of carbon monoxide with an alcohol. As catalysts, preference is given to using alkali metal salts. The objective of US 2004/0171704 is to make the reaction of carbon monoxide with the alcohol possible even in the presence of water and/or carbon dioxide. Catalysts described are alkali metal carbonates, alkali metal nitrates, alkali metal phosphates, alkali metal acetates and alkali metal formates. The use of alkali metal alkoxides is explicitly ruled out since these are deactivated in the presence of water and/or carbon dioxide.

EP 0 596 483 describes a process for preparing methyl formate by carbonylation of methanol in the presence of sodium methoxide or potassium methoxide as catalyst. EP 0 596 483, too, states that the alkali metal methoxide (alkali metal methylate) used as catalyst is converted into inactive decomposition products such as sodium formate or potassium formate, sodium carbonate or potassium carbonate and sodium hydrogencarbonate or potassium hydrogencarbonate. The decomposition products are removed periodically by means of a filter, with about 0.9% by weight of decomposition products occurring at the reactor outlet. The decomposition products are composed of about 38% by weight of sodium formate, 42% by weight of sodium hydrogencarbonate, 15% by weight of sodium carbonate and 6% by weight of sodium methoxide. To reduce catalyst consumption and increase the space-time yield, the reaction is carried out in the presence of a specific sodium or potassium oxaperfluoroalkanesulfonate and a strong organic base.

Disadvantages of the processes described in the prior art are that very high pressures are required in order to achieve acceptable space-time yields and/or recirculations, which are complicated in terms of apparatus, of recycle gas streams having high superficial gas velocities are necessary. These processes require specially designed reactors which are associated with high capital cost. Although relatively low carbon monoxide partial pressures of 3.0 MPa (30 bar) are possible in the process described in EP 0 596 483, the use of very expensive sodium or potassium oxaperfluoroalkanesulfonates and strong organic bases is necessary.

It was an object of the present invention to provide a process which gives methyl formate in good space-time yields. Furthermore, the process should allow a simpler process procedure than the processes described in the prior art, in particular without the costly high-pressure reactors described in the prior art and without expensive catalyst additives such as potassium oxaperfluoroalkanesulfonates and strong organic bases.

This object is achieved by a process for preparing methyl formate by carbonylation of methanol by means of carbon monoxide in a carbonylation reactor in the presence of a catalyst system comprising alkali metal formate and alkali metal alkoxide to give a reaction mixture ($R_M$) which comprises methyl formate, alkali metal formate, alkali metal alkoxide and possibly unreacted methanol and unreacted carbon monoxide and is taken from the carbonylation reactor, wherein the reaction mixture ($R_M$) comprises at least 0.5% by weight of alkali metal alkoxide based on the total weight of the reaction mixture ($R_M$) and the molar ratio of alkali metal formate to alkali metal alkoxide in the reaction mixture ($R_M$) is greater than 1.

DETAILED DESCRIPTION OF THE INVENTION

Very good space-time yields which are sometimes even above the space-time yields described in the prior art are achieved in the process of the invention for preparing methyl formate from methanol and carbon monoxide. The process of the invention has the disadvantage that it makes it possible to obtain methyl formate in good yields even at relatively low pressures. This enables costs to be saved in reactor design. In addition, the process of the invention gives very good space-time yields without the use of expensive additives such as potassium oxaperfluoroalkanesulfonates and strong organic bases being necessary. The problems of salt deposits, which can lead to blockages in pipes and valves, described in the prior art can also be reduced or even completely prevented by the process of the invention.

In the prior art, there was the established belief that only alkali metal alkoxides are catalytically active in respect of the carbonylation of methanol. On the other hand, alkali metal formates are described as catalytically inactive in the prior art. In the prior art, alkali metal formates are also described as consumed catalysts which have to be removed from the reaction mixture and replaced by fresh, catalytically active alkali metal alkoxide.

It has surprisingly been found that alkali metal formate in combination with alkali metal alkoxide is catalytically active in respect of the carbonylation of methanol, contrary to the established belief in the prior art. This applies in particular to a mixture comprising alkali metal formate and alkali metal alkoxide in a molar ratio of alkali metal formate to alkali metal alkoxide of greater than 1, preferably greater than 2, particularly preferably greater than 3 and in particular greater than 5.

The present invention therefore also provides for the use of a mixture which comprises an alkali metal formate and an alkali metal alkoxide and in which the molar ratio of alkali metal formate to alkali metal alkoxide is greater than 1, preferably greater than 2, particularly preferably greater than 3 and in particular greater than 5 as catalyst system for preparing methyl formate by carbonylation of methanol by means of carbon monoxide.

Reaction of Methanol with Carbon Monoxide to Form Methyl Formate

The carbon monoxide used in the process of the invention can be used in solid, liquid or gaseous form. Carbon monoxide can be used as pure material, i.e. having a content of at least 95% by weight, preferably at least 97% by weight and particularly preferably at least 99% by weight. Carbon monoxide is preferably used in gaseous form. The carbon monoxide used is preferably very largely free of carbon dioxide, i.e. generally comprises less than 1% by weight of carbon dioxide, preferably less than 0.5% by weight of carbon dioxide, in each case based on the total weight of the gas mixture comprising carbon monoxide. It is also possible to use gas mixtures which comprise carbon monoxide and in addition to carbon monoxide comprise further inerts such as nitrogen, hydrogen, methane or noble gases. However, the content of inerts is generally below 10% by weight, based on the total weight of the gas mixture comprising carbon monoxide. Although larger amounts may likewise be tolerable, they generally require the use of relatively high pressures, as a result of which additional compression energy is required. The carbon monoxide generally comes from the carbon monoxide sources with which a person skilled in the art will be familiar, for example synthesis gas.

The methanol used in the process of the invention is, in a preferred embodiment, essentially water-free, i.e. the methanol used comprises not more than 250 ppm by weight, preferably not more than 100 ppm by weight and particularly preferably not more than 50 ppm by weight, of water, in each case based on the total weight of methanol used and the water comprised therein.

In a preferred embodiment, the carbonylation of methanol by means of carbon monoxide is carried out in the absence of water. For the purposes of the present invention, in the absence of water means that the reaction mixture ($R_M$) comprises not more than 250 ppm by weight, preferably not more than 100 ppm by weight and particularly preferably not more than 50 ppm by weight, of water, in each case based on the total weight of the reaction mixture ($R_M$).

The alkali metal alkoxide used in the process of the invention can be used as solid or as a solution in a suitable solvent. It is possible to use mixtures of two or more alkali metal alkoxides. For the purposes of the present invention, the term alkali metal alkoxide encompasses both one alkali metal alkoxide and also mixtures of two or more alkali metal alkoxides. However, preference is given to using only one alkali metal alkoxide. In a preferred embodiment, an alkali metal methoxide dissolved in methanol is used.

The alkali metal formate used in the process of the invention can likewise be used as solid or as a solution in a suitable solvent. It is possible to use mixtures of two or more alkali metal formates. For the purposes of the present invention, the term alkali metal formate encompasses both one alkali metal formate and also mixtures of two or more alkali metal formates. However, preference is given to using only one alkali metal formate. In a preferred embodiment, an alkali metal formate dissolved in methanol is used. The alkali metal formate can also be fed to the carbonylation reactor by recirculation from downstream work-up stages.

The alkali metal components of the alkali metal formate and of the alkali metal alkoxide can be selected independently from the group consisting of lithium, sodium, potassium, rubidium and cesium. The alkali metal formate can therefore be selected from the group consisting of lithium formate, sodium formate, potassium formate, rubidium formate and cesium formate. The alkali metal formate is preferably selected from the group consisting of sodium formate and potassium formate. Particular preference is given to potassium formate. The alkali metal alkoxide can be selected from the group consisting of lithium alkoxide, sodium alkoxide, potassium alkoxide, rubidium alkoxide and cesium alkoxide. The alkali metal alkoxide is preferably selected from the group consisting of sodium alkoxide and potassium alkoxide. Particular preference is given to potassium alkoxide.

Suitable alkoxide components of the alkali metal alkoxide are alkoxide anions having from 1 to 12 carbon atoms, for example methoxide, ethoxide, 1-propoxide, 2-propoxide, 1-butoxide, 2-butoxide, 2-methyl-1-propoxide, 2-methyl-2-propoxide, 1-pentoxide, isopentoxide, 1-hexoxide, 1-heptoxide, 1-octoxide, 2-ethyl-1-hexoxide, 1-nonoxide, 3,5,5-trimethyl-1-hexoxide, 2,6-dimethyl-4-heptoxide and 1-decoxide. Particular preference is given to methoxide as alkoxide.

The alkali metal components of the alkali metal formate and of the alkali metal alkoxide are particularly preferably identical.

In particular, the alkali metal formate is potassium formate and the alkali metal alkoxide is potassium methoxide.

In the process of the invention, a mixture of alkali metal formate and alkali metal alkoxide, where the molar ratio of alkali metal formate to alkali metal alkoxide in the mixture is greater than 1, is preferably used as catalyst system. The molar ratio of alkali metal formate to alkali metal alkoxide is preferably in the range from 2 to 20, particularly preferably in the range from 2 to 15, very particularly preferably in the range from 3 to 10 and in particular in the range from 3 to 8, with potassium formate being particularly preferred as alkali metal formate and potassium methoxide being particularly preferred as alkali metal alkoxide.

The molar ratio of alkali metal formate to alkali metal alkoxide in the reaction mixture ($R_M$) is preferably greater than 2, particularly preferably greater than 3 and in particular greater than 5.

The molar ratio of alkali metal formate to alkali metal alkoxide in the reaction mixture ($R_M$) is preferably in the range from 2 to 20, particularly preferably in the range from 2 to 15, very particularly preferably in the range from 3 to 10 and in particular in the range from 3 to 8, with potassium formate being particularly preferred as alkali metal formate and potassium methoxide being particularly preferred as alkali metal alkoxide.

In a preferred embodiment, a catalyst system consisting essentially of the above-described mixture of alkali metal formate and alkali metal alkoxide is used in the process of the invention, with a mixture consisting essentially of potassium formate and potassium methoxide being particularly preferred.

This means that generally not more than 1% by weight, preferably not more than 0.5% by weight and particularly preferably not more than 0.1% by weight and in particular none of further catalytically active substances which catalyze the carbonylation of methanol by means of carbon monoxide are used in addition to the mixture of alkali metal formate and alkali metal alkoxide used as catalyst system in the process of the invention, in each case based on the total weight of the mixture used as catalyst system and any further catalytically active substances present. In a preferred embodiment, the mixture used as catalyst system consists of alkali metal formate and alkali metal alkoxide, with a mixture consisting of potassium formate and potassium methoxide being particularly preferred.

In a preferred embodiment of the process of the invention, no alkali metal oxaperfluorosulfonates and also no strong organic bases having a $pK_a$ of greater than 8.7 are present. Examples of alkali metal oxaperfluorosulfonates which are not present in the process of the invention are those of the general formula $$CF_3CF_2(OCFXCF_2)_pOCF_2SO_3M$$

where p=0 to 2, X=F, $CF_3$ and M=Na, K.

The present invention therefore also provides for the use of a mixture of an alkali metal formate and an alkali metal alkoxide as catalyst system for the reaction of methanol with carbon monoxide to form methyl formate, wherein the molar ratio of alkali metal formate to alkali metal alkoxide in the mixture is greater than 1. The abovementioned preferences in respect of the alkali metal formate and the alkali metal alkoxide and also the molar ratios apply analogously to the use according to the invention of the mixture.

As carbonylation reactors in the process of the invention, it is in principle possible to use all reactors which are suitable for gas/liquid reactions. Suitable standard reactors for gas-liquid reaction systems are indicated, for example, in K. D. Henkel, "Reactor Types and Their Industrial Applications", in Ullmann's Encyclopedia of Industrial Chemistry, 2005, Wiley-VCH-Verlag GmbH & CO. KGaA, DOI: 10.1002/14356007.b04_087, chapter 3.3 "Reactors for gas-liquid reactions". Examples which may be mentioned are stirred tank reactors, tube reactors, jet loop reactors or bubble columns.

The carbonylation of methanol by means of carbon monoxide can be carried out continuously or batchwise in the process of the invention. In the batchwise mode of operation, the carbonylation reactor is charged with the desired liquid and optionally solid starting materials and auxiliaries and is subsequently pressurized with carbon monoxide to the desired pressure at the desired temperature. After the reaction is complete, the carbonylation reactor is normally depressurized. In the continuous mode of operation, methanol, carbon monoxide, the catalyst system (alkali metal formate and alkali metal alkoxide, preferably alkali metal methoxide and alkali metal formate) are fed continuously into the carbonylation reactor.

Accordingly, the reaction mixture ($R_M$) is discharged continuously from the carbonylation reactor so that the liquid level in the carbonylation reactor remains the same on average. The continuous carbonylation of methanol by means of carbon monoxide is, preferred.

A liquid phase and a gas phase are generally present in the carbonylation reactor. The carbonylation reaction generally takes place in the liquid phase.

According to the present invention, the reaction mixture ($R_M$) is the fraction which is liquid under the reaction conditions of the carbonylation and is taken off from the carbonylation reactor.

The reaction mixture ($R_M$) thus describes the composition of the liquid phase which is taken off from the carbonylation reactor under the reaction pressure of the carbonylation, i.e. before depressurization.

The carbonylation reaction of methanol with carbon monoxide generally takes place in the liquid phase at a total pressure in the range from 30 to 100 bar, preferably in the range from 30 to 70 bar and particularly preferably in the range from 50 to 65 bar, and at a temperature in the range from 60 to 140° C., preferably in the range from 65 to 110° C. and particularly preferably in the range from 70 to 100° C., in the carbonylation reactor. In a very particularly preferred embodiment, the carbonylation in the carbonylation reactor is carried out at a temperature in the range from 70 to 100° C. and a total pressure in the range from 50 to 65 bar.

The molar feed ratio of the amount of methanol fed into the carbonylation reactor to the amount of carbon monoxide fed into the carbonylation reactor is generally from 1 to 5, preferably from 2 to 5, particularly preferably from 2.5 to 4 and in particular from 3 to 4, in the process of the invention. The amount of methanol fed into the carbonylation reactor is made up of the freshly introduced methanol and any methanol recirculated from downstream work-up stages. The amount of carbon monoxide fed into the carbonylation reactor is made up of the freshly introduced carbon monoxide and any carbon monoxide recirculated from downstream work-up stages.

The molar feed ratio of the amount of methanol fed into the carbonylation reactor to the amount of alkali metal alkoxide, preferably potassium methoxide, fed into the carbonylation reactor is generally from 100 to 400, preferably from 150 to 350, particularly preferably from 200 to 350 and in particular from 230 to 330, in the process of the invention. The amount of alkali metal alkoxide fed into the carbonylation reactor is made up of the freshly introduced alkali metal alkoxide and any alkali metal alkoxide recirculated from downstream work-up stages.

The molar feed ratio of the amount of methanol fed into the carbonylation reactor to the amount of alkali metal formate, preferably potassium formate, fed into the carbonylation reactor is generally from 25 to 400, preferably from 30 to 200, particularly preferably from 30 to 100 and in particular from 30 to 50, in the process of the invention. The amount of alkali metal formate fed into the carbonylation reactor is made up of the freshly introduced alkali metal formate and any alkali metal formate recirculated from downstream work-up stages.

For the purposes of the present invention, "freshly introduced" in respect of methanol, carbon monoxide, alkali metal alkoxide and alkali metal formate refers to the components which are not recirculated from downstream work-up stages. These are components which do not originate from the process of the invention but are instead introduced from outside into the process of the invention.

However, the addition of freshly introduced alkali metal formate is not absolutely necessary. Alkali metal formate is formed according to the above-described secondary reactions (i) and/or (ii) during the carbonylation of methanol. In a preferred embodiment of the process of the invention, no fresh alkali metal formate is introduced into the carbonylation reactor and the alkali metal formate originates exclusively from the alkali metal formate recirculated from a downstream work-up stage. In this embodiment, the alkali metal formate accumulates in the process of the invention until the concentration according to the invention of alkali metal formate is reached in the reaction mixture ($R_M$).

Alkali metal alkoxide and alkali metal formate are preferably introduced as a solution in methanol into the reactor.

In the process of the invention, a reaction mixture ($R_M$) comprising methyl formate, alkali metal formate, alkali metal alkoxide and also any unreacted methanol and unreacted carbon monoxide is taken off from the carbonylation reactor. The composition of the reaction mixture ($R_M$) in respect of the alkali metal formate and alkali metal alkoxide comprised therein depends on the catalyst system used. The information and preferences indicated above for the catalyst system apply analogously to the composition of the reaction mixture ($R_M$) in respect of the alkali metal formate and alkali metal alkoxide comprised therein.

In a preferred embodiment, a mixture which consists essentially of potassium formate and potassium methoxide is used as catalyst system, giving a reaction mixture ($R_M$) consisting essentially of methyl formate, potassium formate and potassium methoxide and also any unreacted methanol and any unreacted carbon monoxide. For the purposes of the present invention, "consists essentially of" in respect of the reaction mixture ($R_M$) means that the reaction mixture ($R_M$) comprises not more than 1% by weight, preferably not more than 0.5% by weight, of further components in addition to methyl formate, alkali metal formate, alkali metal methoxide and any unreacted methanol and unreacted carbon monoxide, in each case based on the total weight of the reaction mixture ($R_M$).

In general, the molar ratio of alkali metal formate to alkali metal alkoxide in the reaction mixture ($R_M$) which is taken off from the carbonylation reactor is greater than 1. The molar ratio of alkali metal formate to alkali metal alkoxide in, the reaction mixture ($R_M$) is preferably in the range from 2 to 20, particularly preferably in the range from 2 to 15, very particularly preferably in the range from 4 to 12 and in particular in the range from 5 to 10, with potassium formate being particularly preferred as alkali metal formate and potassium methoxide being particularly preferred as alkali metal alkoxide.

The concentration of the alkali metal alkoxide, preferably the potassium methoxide, in the reaction mixture ($R_M$) is generally at least 0.5% by weight based on the total weight of the reaction mixture ($R_M$). The concentration of the alkali metal alkoxide in the reaction mixture ($R_M$) is preferably in the range from 0.5 to 1.5% by weight, more preferably in the range from 0.5 to 1.0% by weight and particularly preferably in the range from 0.55 to 0.9% by weight, in each case based on the total weight of the reaction mixture ($R_M$).

The concentration of the alkali metal alkoxide, preferably the potassium methoxide, in the reaction mixture ($R_M$) is generally at least 0.5% by weight based on the total weight of the reaction mixture ($R_M$). The concentration of the alkali metal alkoxide in the reaction mixture ($R_M$) is preferably >0.5% by weight, particularly preferably at least 0.51% by weight, based on the total weight of the reaction mixture ($R_M$). The concentration of the alkali metal alkoxide in the reaction mixture ($R_M$) is preferably in the range from >0.5 to 1.5% by weight, more preferably in the range from >0.5 to 1.0% by weight and particularly preferably in the range from 0.51 to 0.9% by weight, in particular in the range from 0.55 to 0.9% by weight, in each case based on the total weight of the reaction mixture ($R_M$).

The concentration of the alkali metal formate, preferably the potassium formate, in the reaction mixture ($R_M$) is generally at least 2.25% by weight based on the total weight of the reaction mixture ($R_M$). The concentration of the alkali metal formate is preferably in the range from 2.5 to 15% by weight, preferably in the range from 3 to 10% by weight and particularly preferably in the range from 5 to 7.5% by weight, in each case based on the total weight of the reaction mixture ($R_M$).

The percent by weight indicated above for the concentrations of the alkali metal formate and of the alkali metal methoxide in the reaction mixture ($R_M$) are subject to the condition that the molar ratio of alkali metal formate to alkali metal alkoxide in the reaction mixture ($R_M$) is greater than 1.

In a particularly preferred embodiment, a reaction mixture ($R_M$), where the reaction mixture ($R_M$) comprises from 0.5 to 1.5% by weight of alkali metal alkoxide and from 2.5 to 15% by weight of alkali metal formate, in each case based on the total weight of the reaction mixture ($R_M$), is obtained in the process of the invention.

In a particularly preferred embodiment, a reaction mixture ($R_M$), where the reaction mixture ($R_M$) comprises from 0.51 to 1.5% by weight of alkali metal alkoxide and from 2.5 to 15% by weight of alkali metal formate, in each case based on the total weight of the reaction mixture ($R_M$), is obtained in the process of the invention.

The reaction mixture ($R_M$) generally comprises not more than 48% by weight of methyl formate, based on the total weight of the reaction mixture ($R_M$). The reaction mixture ($R_M$) preferably comprises from 12 to 45% by weight of methyl formate, more preferably from 25 to 45% by weight and in particular from 35 to 45% by weight, in each case based on the total weight of the reaction mixture ($R_M$).

The reaction mixture ($R_M$) generally comprises unreacted methanol. The reaction mixture ($R_M$) preferably comprises from 40 to 85% by weight of methanol, more preferably from 45 to 60% by weight and in particular from 45 to 55% by weight, in each case based on the total weight of the reaction mixture ($R_M$).

In a preferred embodiment of the process of the invention, the reaction mixture ($R_M$) comprises
from 12 to 45% by weight of methyl formate,
from 40 to 85% by weight of methanol,
from 2.5 to 15% by weight of alkali metal formate,
from 0.5 to 1.5% by weight of alkali metal alkoxide and
from 0 to 2% by weight of carbon monoxide,
where the sum of all components comprised in the reaction mixture ($R_M$) is 100% by weight and the reaction mixture ($R_M$) comprises not more than 1% by weight, preferably not more than 0.5% by weight, of further components other than methyl formate, methanol, alkali metal formate, alkali metal alkoxide, carbon monoxide and water, in each case based on the total weight of the reaction mixture ($R_M$).

In a particularly preferred embodiment of the process of the invention, the reaction mixture ($R_M$) comprises
from 35 to 45% by weight of methyl formate,
from 45 to 62% by weight of methanol,
from 2.5 to 7.5% by weight of potassium formate,
from 0.5 to 0.8% by weight of potassium methoxide and
from 0 to 1.5% by weight of carbon monoxide,
where the sum of all components comprised in the reaction mixture ($R_M$) is 100% by weight and the reaction mixture ($R_M$) comprises not more than 1% by weight, preferably not more than 0.5% by weight, of further components other than methyl formate, methanol, potassium formate, potassium methoxide, carbon monoxide and water, in each case based on the total weight of the reaction mixture ($R_M$).

Further components which can be comprised in the above amounts in the reaction mixture ($R_M$) are, for example, impurities in the starting materials, e.g. nitrogen, argon, hydrogen or methane from the carbon monoxide used and impurities such as formaldehyde and formaldehyde dimethyl acetal from the methanol used and also impurities comprised in the alkoxides and formates used and by-products from the carbonylation of methanol, e.g. dimethyl ether and methyl glyoxal methyl hemiacetal.

In a preferred embodiment, the liquid feed fed into the carbonylation reactor is composed essentially of methanol, alkali metal alkoxide and alkali metal formate and optionally methyl formate. In a preferred embodiment, the liquid feed comprises not more than 1% by weight, preferably not more than 0.5% by weight, of components other than methanol, alkali metal methoxide and alkali metal formate and optionally methyl formate, in each case based on the total weight of the liquid feed.

For the present purposes, the term liquid feed encompasses all liquid components fed into the reactor, i.e. the sum of freshly introduced and recirculated liquid components.

The composition of the reaction mixture ($R_M$) can be controlled via the above-described feed ratios of carbon monoxide, methanol and catalyst system (alkali metal formate and alkali metal alkoxide).

The amount of methyl formate comprised in the reaction mixture ($R_M$) is made up of the amount of methyl formate which is formed from carbon monoxide and methanol in the carbonylation reactor and the amount of methyl formate which is optionally recirculated from a downstream work-up step to the carbonylation reactor.

The amount of carbon monoxide and methanol comprised in the reaction mixture ($R_M$) is controlled via the feed ratios of carbon monoxide to methanol and via the reaction of carbon monoxide with methanol to form methyl formate in the carbonylation reactor and also via the reaction pressure of the carbonylation.

The setting of the composition of the reaction mixture ($R_M$) can be carried out by conventional methods of regulation known to those skilled in the art, for example by means of a measuring unit which measures the composition of the reaction mixture ($R_M$) taken off from the carbonylation reactor and in the event of a deviation from the intended composition modifies the feed ratios accordingly.

The amounts of alkali metal formate and alkali metal alkoxide comprised in the reaction mixture ($R_M$) are controlled via the amounts of alkali metal formate and alkali metal alkoxide fed into the carbonylation reactor, i.e. via the amount and composition of the catalyst system. Alkali metal formate and alkali metal alkoxide are generally introduced as a solution, preferably a solution in methanol, into the carbonylation reactor.

The catalyst system comprising alkali metal formate and alkali metal alkoxide can be introduced in fresh form from the outside into the carbonylation reactor. In a preferred embodiment, the process of the invention is carried out continuously and the alkali metal formate and alkali metal alkoxide comprised in the catalyst system is recirculated to the carbonylation reactor from a downstream work-up step.

Here, it should be taken into account that the alkali metal alkoxide comprised in the catalyst system is partly converted into alkali metal formate in the carbonylation reactor. This occurs by reaction of alkali metal alkoxide with methyl formate to form alkali metal formate and dimethyl ether and by hydrolysis of alkali metal alkoxide and methyl formate by means of traces of water to form alkali metal formate and methanol. The formation of alkali metal formate is described with the aid of the following reaction equations iii) to v) for the example of the formation of potassium formate from potassium methoxide $$HCOOCH_3 + KOCH_3 \rightarrow HCOOK + CH_3OCH_3 \quad \text{iii)}$$

$$KOCH_3 + H_2O \rightarrow KOH + CH_3OH \quad \text{iv)}$$

$$KOH + HCOOCH_3 \rightarrow HCOOK + CH_3OH \quad \text{v)}$$

To set the composition according to the invention of alkali metal formate and alkali metal alkoxide in the reaction mixture ($R_M$), it is therefore generally necessary to separate off part of the alkali metal formate formed according to the reaction equations iii) to v) from the reaction mixture ($R_M$). In addition, it is generally necessary to replace the alkali metal methoxide which has reacted according to the reaction equations iii) and iv).

The removal of the alkali metal formate formed and the replacement of the alkali metal alkoxide which has reacted can be carried out sequentially or continuously. Preference is given to the alkali metal formate formed being continuously separated off and the alkali metal alkoxide which has reacted being continuously replaced by alkali metal alkoxide freshly introduced from the outside.

In a particularly preferred embodiment, the reaction mixture ($R_M$) taken off from the carbonylation reactor is subjected to a further work-up comprising the following steps:
(a) separation of carbon monoxide from the reaction mixture (RM) in a separation apparatus to give a gas stream (G1) comprising carbon monoxide and a liquid stream (L1) comprising methyl formate, alkali metal formate, alkali metal alkoxide and methanol,
(b) separation of the methyl formate from the liquid stream (L1) in a first distillation apparatus to give a distillate (D1) comprising methyl formate and a bottom mixture (S1) comprising alkali metal formate, alkali metal alkoxide and methanol,
(c) division of the bottom mixture (S1) into a substream (S1a) which is recirculated to the carbonylation reactor and a substream (S1b) and
(d) separation of the methanol from the substream (S1b) in a second distillation apparatus to give a distillate (D2) which comprises methanol and is recirculated to the first distillation apparatus and a bottom mixture (S2) comprising alkali metal formate and alkali metal alkoxide.

The removal of the carbon monoxide in step (a) is not absolutely necessary. It is also possible to feed the reaction mixture ($R_M$) directly to the first distillation apparatus in step (b). If the carbon monoxide is separated off from the reaction mixture ($R_M$), the gas stream (G1) is preferably recirculated to the carbonylation reactor. The removal of the carbon monoxide in step (a) is preferably carried out using a flash apparatus as separation apparatus.

In step (b), the methyl formate can be separated off completely or partly from the liquid stream (L1) or from the reaction mixture ($R_M$).

In the case of partial removal, for example from 50 to 90% by weight of the methyl formate comprised in the liquid stream (L1) or of the methyl formate comprised in the reaction mixture ($R_M$), preferably from 60 to 90% by weight and more preferably from 80 to 90% by weight, are separated off, in each case based on the total weight of the methyl formate comprised in the liquid stream (L1) or of the methyl formate comprised in the reaction mixture ($R_M$).

In a further embodiment of the process of the invention, the methyl formate is completely separated off in the first distillation apparatus in process step (b). For the purposes of the present invention, "completely separated off" means removal of more than 90% of the methyl formate comprised in the liquid stream (L1) or of the methyl formate comprised in the reaction mixture ($R_M$), preferably more than 98.5%, particularly preferably more than 99%, in particular more than 99.5%, in each case based on the total amount of the methyl formate comprised in the liquid stream (L1) or of the methyl formate comprised in the reaction mixture ($R_M$).

In the partial removal of the methyl formate, the bottom mixture (S1) still comprises methyl formate. In the case of the complete removal of the methyl formate, the bottom mixture (S1) is very largely free of methyl formate. The complete removal of the methyl formate is preferred.

The removal of the methyl formate can, for example, be carried out in an evaporator or in a distillation unit comprising vaporizer and column, with the column being filled with ordered packing, random packing elements and/or plates.

The distillate (D1) separated off in step (b) can still comprise methanol in addition to methyl formate. In a preferred embodiment, the distillate (D1) comprises from 60 to 97% by weight of methyl formate and from 3 to 40% by weight of methanol, preferably from 75 to 85% by weight of methyl formate and from 15 to 25% by weight of methanol. The distillate (D1) can be worked up further, for example by distillation. The methanol separated off can be recirculated to the carbonylation reactor. The recirculated methanol can comprise methyl formate.

It is also possible for the methyl formate to be reacted further. The methyl formate can, for example, be hydrolyzed to formic acid. The methanol formed here can likewise be recirculated to the carbonylation reactor. The recirculated methanol can comprise methyl formate.

The removal of the methyl formate in step (b) gives a bottom mixture (S1) comprising alkali metal formate, alkali metal alkoxide and methanol. Alkali metal formate and alkali metal alkoxide are preferably present as a solution in methanol in the bottom mixture (S1).

The control of the amounts of alkali metal formate and alkali metal alkoxide comprised in the reaction mixture ($R_M$) is, in a preferred embodiment, effected by dividing the bottom mixture (S1) into the substreams (S1a) and (S1b).

The separation of the alkali metal formate formed from the reaction mixture ($R_M$) is effected via the substream (S1b). The amount of substream (S1b) separated off controls the accumulation of the alkali metal formate in the reaction mixture ($R_M$). To discharge the alkali metal formate formed, the substream (S1b) is fed to the second distillation apparatus. To set the composition according to the invention of the reaction mixture ($R_M$), the bottom mixture (S1) is divided in such a way that the weight ratio of the substream (S1a) to the substream (S1b) is greater than 50:1, preferably greater than 100:1.

In other words, this means that at least 50 parts by weight of substream (S1a), preferably at least 100 parts by weight of substream (S1a), per part by weight of substream (S1b) discharged are recirculated to the carbonylation reactor.

At the bottom of the second distillation apparatus, a bottom mixture (S2) comprising alkali metal formate and alkali metal methoxide is obtained. To prevent precipitation of solids and to minimize the risk of encrustations or blockages in the bottom of the second distillation apparatus, water is preferably introduced into the second distillation apparatus in a preferred embodiment. The water can, for example, be fed as steam or steam condensate into the second distillation apparatus.

In this embodiment, the work-up of the reaction mixture ($R_M$) comprises the following steps:

(a) separation of carbon monoxide from the reaction mixture ($R_M$) in a separation apparatus to give a gas stream (G1) comprising carbon monoxide and a liquid stream (L1) comprising methyl formate, alkali metal formate, alkali metal alkoxide and methanol, (b) separation of the methyl formate from the liquid stream (L1) in a first distillation apparatus to give a distillate (D1) comprising methyl formate and a bottom mixture (S1) comprising alkali metal formate, alkali metal alkoxide and methanol, (c) division of the bottom mixture (S1) into a substream (S1a) which is recirculated to the carbonylation reactor and a substream (S1b) and (d) separation of the methanol from the substream (S1b) in a second distillation apparatus into which water is introduced to give a distillate (D2) which comprises methanol and is recirculated to the first distillation apparatus and a bottom mixture (S2w) comprising alkali metal hydroxide, alkali metal formate and water.

The water can, for example, be fed as steam or steam condensate into the second distillation apparatus. The water is, in a preferred embodiment, introduced into the bottom of the second distillation apparatus.

The addition of water leads to the alkali metal alkoxide being hydrolyzed to the corresponding alkali metal hydroxide and the corresponding alcohol. In the case of the preferred potassium methoxide, this is hydrolyzed to potassium hydroxide and methanol. The methanol formed in this way is likewise separated off as distillate (D2) at the top of the second distillation apparatus and is preferably recirculated to the first distillation apparatus.

Since not only alkali metal formate but also alkali metal alkoxide are separated off via the substream (S1b), fresh alkali metal alkoxide has to be introduced from the outside into the carbonylation reactor. The introduction of the alkali metal alkoxide from the outside into the carbonylation reactor is carried out continuously in a preferred embodiment. The freshly introduced alkali metal alkoxide can be introduced as solid but is preferably introduced as a solution in methanol into the carbonylation reactor. The freshly introduced alkali metal alkoxide can be fed as a separate stream into the carbonylation reactor. It is also possible to mix the freshly introduced alkali metal alkoxide into the substream (S1a) recirculated from step (c) to the carbonylation reactor.

The present invention is illustrated by the following figures and the following examples without being restricted thereto.

Figure 1:
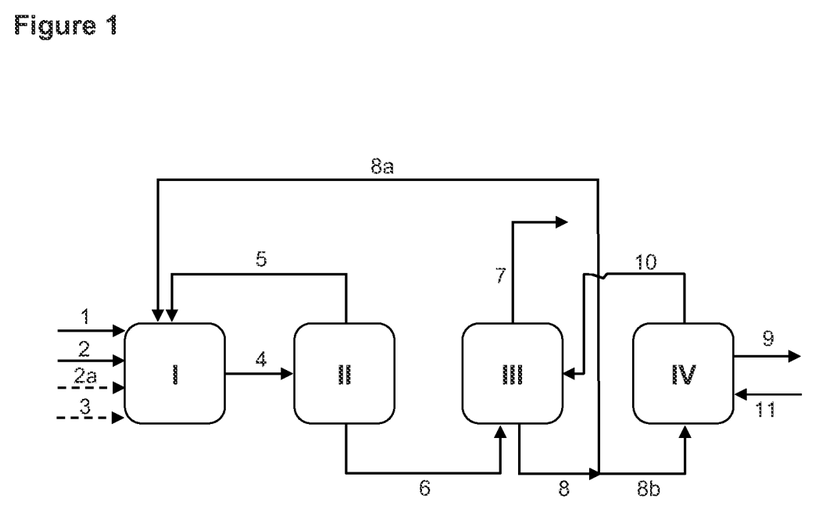
FIG. 1 shows a block diagram of a preferred embodiment of the process of the invention.

FIG. 1 shows a block diagram of a preferred embodiment of the process of the invention. In FIG. 1, the reference numerals have the following meanings:

1 stream comprising carbon monoxide
2 stream comprising methanol
2a stream which comprises methanol and is recirculated from a downstream work-up stage
3 stream comprising alkali metal alkoxide dissolved in methanol
4 stream comprising methyl formate, alkali metal formate, alkali metal alkoxide and possibly unreacted methanol and unreacted carbon monoxide; corresponds to reaction mixture ($R_M$)
5 stream comprising carbon monoxide; corresponds to gas stream (G1)
6 stream comprising methyl formate, alkali metal formate, alkali metal alkoxide and methanol; corresponds to liquid stream (L1)
7 stream comprising methyl formate and possibly methanol; corresponds to distillate (D1)
8 stream comprising alkali metal formate, alkali metal alkoxide and methanol; corresponds to bottom mixture (S1)
8a stream comprising alkali metal formate, alkali metal alkoxide and methanol; corresponds to substream (S1a)
8b stream comprising alkali metal formate, alkali metal alkoxide and methanol; corresponds to substream (S1b)
9 stream comprising alkali metal formate, alkali metal hydroxide and water; corresponds to bottom mixture (S2w)
10 stream comprising methanol; corresponds to distillate (D2)
11 stream comprising water
I carbonylation reactor
II separation apparatus
III first distillation apparatus
IV second distillation apparatus Carbon monoxide, methanol and the catalyst system comprising alkali metal formate and alkali metal alkoxide are fed into the carbonylation reactor I. In the carbonylation reactor, methanol is reacted with carbon monoxide to form methyl formate, giving the reaction mixture ($R_M$). The carbon monoxide is fed in via stream 1 (carbon monoxide freshly introduced from the outside) and stream 5 (carbon monoxide recirculated from the separation apparatus II). The alkali metal formate and the alkali metal alkoxide are recirculated as stream 8a (corresponds to substream S1a) from the bottom of the first distillation apparatus III to the carbonylation reactor. The stream 8a comprises methanol, the alkali metal formate and the alkali metal alkoxide, preferably in dissolved form.

Losses of alkali metal alkoxide can if necessary be compensated via stream 3. Stream 3 preferably comprises alkali metal alkoxide dissolved in methanol. Methanol is preferably fed into the carbonylation reactor via the streams 2 and/or 2a. Stream 2 describes the case of fresh methanol being introduced from the outside. However, it is also possible, as an alternative or in addition, to introduce the methanol via stream 2a which originates from later work-up stages or the reactions of the methyl formate.

A reaction mixture ($R_M$) is obtained in the carbonylation reactor I and is taken off from the carbonylation reactor I and conveyed as stream 4 to the separation apparatus II. In the separation apparatus II, unreacted carbon monoxide is separated off from the reaction mixture ($R_M$). This is preferably carried out by depressurization of the reaction mixture ($R_M$). A gas stream (G1) which consists essentially of carbon monoxide is obtained in the separation apparatus II and is recirculated as stream 5 to the carbonylation reactor I.

A liquid stream (L1) comprising methyl formate, alkali metal formate, alkali metal alkoxide and methanol is taken off from the separation apparatus II and is conveyed as stream 6 to the first distillation apparatus III. In the first distillation apparatus III, a stream 7 comprising methyl formate is separated off at the top of this distillation apparatus (distillate (D1)). It is also possible to separate off a mixture of methyl formate and methanol at the top of the first distillation apparatus III. In a preferred embodiment, the stream 7 is reacted further. Preference is given to hydrolyzing the methyl formate to formic acid. The methanol formed in the hydrolysis can be recirculated as stream 2a to the carbonylation reactor I. At the bottom of the first distillation apparatus III, a bottom mixture (S1) comprising alkali metal formate, alkali metal alkoxide and methanol is obtained. The bottom mixture (S1) is taken off as stream 8 from the distillation apparatus III. The stream 8 is divided into a substream 8a and a substream 8b. The substream 8a (corresponds to substream S1a) is recirculated to the carbonylation reactor I. The stream 8b (corresponds to substream S1b) is worked up further in the second distillation apparatus IV. Water is fed as stream 11 into the second distillation apparatus IV. Stream 11 is preferably fed into the bottom of the second distillation apparatus IV. In the second distillation apparatus IV, the alkali metal alkoxide comprised in stream 8b is hydrolyzed to the corresponding alkali metal hydroxide and the corresponding alcohol. In the case of the potassium methoxide which is preferably comprised in stream 8b, potassium hydroxide and methanol are formed in the hydrolysis. Methanol is taken off as stream 10 at the top of the second distillation apparatus IV and is recirculated to the first distillation apparatus III. An aqueous solution comprising potassium hydroxide, potassium formate and water is taken off as stream 9 from the second distillation apparatus IV.

Figure 2:
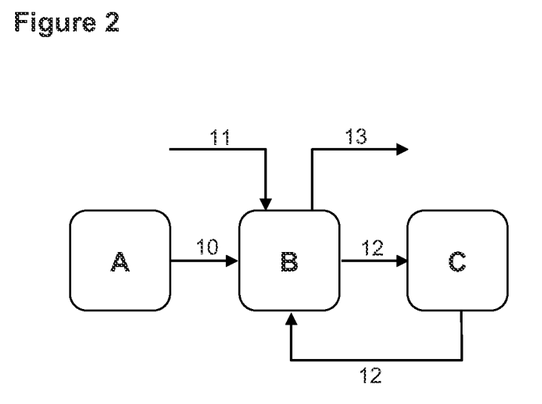
FIG. 2 shows a laboratory apparatus in which the process of the invention is carried out.

FIG. 2 shows a laboratory apparatus in which the process of the invention is carried out. In FIG. 2, the reference symbols have the following meanings:

A reservoir comprising a mixture of methanol, potassium methoxide and optionally an alkali metal formate
B carbonylation reactor
C On-line ATR-FIR measurement sensor (ATR-MIR, Matrix MF from Bruker)
10 stream comprising methanol, potassium methoxide and optionally an alkali metal formate
11 stream comprising carbon monoxide
12 stream comprising methyl formate, possibly alkali metal formate, potassium methoxide, methanol and possibly unreacted carbon monoxide
13 stream comprising methyl formate, possibly alkali metal formate, potassium methoxide, methanol and possibly unreacted carbon monoxide; corresponds to reaction mixture ($R_M$).

The invention is illustrated below with the aid of examples, without being restricted thereto.

The experiments on the carbonylation of methanol by means of carbon monoxide were carried out in the laboratory apparatus shown in FIG. 2. A mixture of methanol, potassium methoxide and optionally an alkali metal formate was placed in the reservoir A. The carbonylation reactor was simulated by an HC steel autoclave having a volume of 270 ml. The reactor volume of the autoclave was separated by means of a riser tube into a 150 ml liquid phase and a 120 ml gas phase. Heating was effected by means of an oil bath. The temperature was regulated by means of a thermocouple.

Methanol and the catalyst system are fed continuously from the reservoir A into the carbonylation reactor (B) (see stream 10 in FIG. 2). Carbon monoxide is fed in via stream 11. For analysis, a stream 12 is taken off from the carbonylation reactor (B) and conveyed via an on-line ATR-FIR measurement sensor back to the carbonylation reactor (B). The ATR-FIR measurement sensor (C) has a calibration from 0 to 80% by weight of methyl formate in methanol. In the measurement sensor, a measurement point was determined every 60 seconds, for which purpose the average of 64 individual measurements was formed.

The composition of the mixture comprised in the reservoir A and the composition of the reaction mixture ($R_M$) obtained in the experiments is reported in the following examples.

Comparative Example 1

The comparative example was carried out in the laboratory plant shown in FIG. 2. Firstly, the entire laboratory plant was made inert by means of nitrogen. Likewise under nitrogen, 1400 g of a solution composed of 99.2% by weight of methanol and 0.8% by weight of potassium methoxide was made up and transferred under nitrogen into the reservoir (A) which stood on a balance. 555 g/h of this mixture were pumped continuously as stream (10) into the autoclave (B) from below. 188 standard l/h of carbon monoxide (purity 99.97% by volume) were fed as stream (11) into the carbonylation reactor on the lid side. Autoclave (B) was vigorously stirred at 750 revolutions per minute and operated at 85° C. The two-phase reaction mixture ($R_M$) is continuously discharged as stream (13) from the carbonylation reactor via the riser tube. The pressure in the carbonylation reactor was maintained at 55 bar by means of a pressure regulating valve in the discharge line. For the on-line analysis, 80 l/h of the reaction mixture ($R_M$) were conveyed continuously as stream (12) by means of a pump from the carbonylation reactor. Stream (12) was cooled to 30° C., subsequently pumped through an ATR-FIR sensor (C) and from there conveyed back into the carbonylation reactor. After 1 hour, a steady-state methyl formate content in the reactor of 10.5% by weight was measured.

Example 2

Example 2 was carried out in a manner analogous to comparative example 1. As feed, 1400 g of a solution composed of 96.7% by weight of MeOH, 0.8% by weight of potassium methoxide and 2.5% by weight of potassium formate were introduced under nitrogen into reservoir (A). The experimental procedure and the experimental parameters were analogous to comparative example 1. After 1 hour of carrying out the experiment, a steady-state methyl formate content in the reactor of 12.8% by weight was measured.

It can be seen from example 2 that the formation of methyl formate can be increased by 22% under otherwise identical reaction conditions by use of 2.5% by weight of potassium formate in the feed.

Example 3

Example 3 was carried out in a manner analogous to comparative example 1. As feed, 1400 g of a solution composed of 94.2% by weight of MeOH, 0.8% by weight of potassium methoxide and 5.0% by weight of potassium formate were introduced under nitrogen into reservoir (A). The experimental procedure and the experimental parameters selected were analogous to comparative example 1. After 1 hour of carrying out the experiment, a steady-state methyl formate content in the reactor of 13.3% by weight was measured.

It can be seen from example 3 that the formation of methyl formate can be increased further compared to example 2 under otherwise identical reaction conditions by use of 5% by weight of potassium formate.

Comparative Example 4

Comparative example 4 was carried out in the laboratory plant shown in FIG. 2. Firstly, the entire laboratory plant was made inert by means of nitrogen. Likewise under nitrogen as protective gas, 850 g of a solution composed of 99.3% by weight of methanol and 0.7% by weight of potassium methoxide was made up and transferred under nitrogen into the reservoir (A) which stood on a balance. 480 g/h of this mixture were pumped continuously as stream (10) into the autoclave (B) from below. 155 standard l/h of carbon monoxide (purity 99.97% by volume) were fed as stream (11) into the carbonylation reactor on the lid side. Autoclave (B) was vigorously stirred at 750 revolutions per minute and operated at 85° C. The two-phase reaction mixture ($R_M$) is continuously discharged as stream (13) from the carbonylation reactor via the riser tube. The pressure in the reactor was maintained at 55 bar by means of a pressure regulating valve in the discharge line. For the on-line analysis, 80 l/h of the reaction mixture ($R_M$) were conveyed continuously as stream (12) by means of a pump from the carbonylation reactor (B). Stream (12) was cooled to 30° C., subsequently pumped through an ATR-FIR sensor (C) and from there conveyed back into the carbonylation reactor (B). After 1 hour, a steady-state methyl formate content in the reactor of 11.6% by weight was measured.

Example 5

Example 5 was likewise carried out in the laboratory plant shown in FIG. 2. As feed, 850 g of a solution composed of 94.3% by weight of MeOH, 0.7% by weight of potassium methoxide and 5.0% by weight of sodium formate were introduced under nitrogen into the reservoir (A). The experimental procedure and the experimental parameters selected were analogous to comparative example 4. After 1 hour of carrying out the experiment, a steady-state methyl formate content in the reactor of 13.0% by weight was measured.

Example 6

Example 6 was likewise carried out in the laboratory plant shown in FIG. 2. As feed, 850 g of a solution composed of 94.3% by weight of MeOH, 0.7% by weight of potassium methoxide and 5.0% by weight of potassium formate were introduced under nitrogen into the reservoir (A). The experimental procedure and the experimental parameters selected were analogous to comparative example 4. After 1 hour of carrying out the experiment, a steady-state methyl formate content in the reactor of 15.2% by weight was measured.

Example 7

Example 7 was likewise carried out in the laboratory plant shown in FIG. 2. As feed, 850 g of a solution composed of 94.3% by weight of MeOH, 0.7% by weight of potassium methoxide and 5.0% by weight of rubidium formate were introduced under nitrogen into reservoir (A). The experimental procedure and the experimental parameters selected were analogous to comparative example 4. After 1 hour of carrying out the experiment, a steady-state methyl formate content in the reactor of 13.6% by weight was measured.

It can be seen from examples 5 to 7 that the formation of methyl formate can be significantly increased compared to comparative example 4 under otherwise identical reaction conditions by addition of 5% by weight of sodium formate, potassium formate and rubidium formate. However, the use of potassium formate is preferred (example 6).

The invention claimed is:

1. A process for preparing methyl formate by carbonylation of methanol by means of carbon monoxide in a carbonylation reactor in the presence of a catalyst system comprising alkali metal formate and alkali metal alkoxide to give a reaction mixture ($R_M$) which comprises methyl formate, alkali metal formate, alkali metal alkoxide and possibly unreacted methanol and unreacted carbon monoxide and is taken from the carbonylation reactor, wherein the reaction mixture ($R_M$) comprises at least 0.5% by weight of alkali metal alkoxide based on the total weight of the reaction mixture ($R_M$) and the molar ratio of alkali metal formate to alkali metal alkoxide in the reaction mixture ($R_M$) is greater than 1.

2. The process according to claim 1, wherein the alkali metal components of the alkali metal formate and the alkali metal alkoxide are selected independently from the group consisting of lithium, sodium, potassium, rubidium and cesium.

3. The process according to claim 1, wherein the alkali metal formate is selected from the group consisting of sodium formate and potassium formate and the alkali metal alkoxide is selected from the group consisting of sodium alkoxide and potassium alkoxide.

4. The process according to claim 1, wherein the alkali metal components of the alkali metal formate and of the alkali metal alkoxide are identical.

5. The process according to claim 1, wherein the alkali metal formate is potassium formate and the alkali metal alkoxide is potassium methoxide.

6. The process according to claim 1, wherein the methanol used comprises not more than 250 ppm by weight, of water, in each case based on the total weight of the methanol used.

7. The process according to claim 1, wherein the methanol used comprises not more than 100 ppm of water based on the total weight of the methanol used.

8. The process according to claim 1, wherein the methanol used comprises not more than 50 ppm by weight of water based on the total weight of the methanol used.

9. The process according to claim 1, wherein the reaction mixture ($R_M$) comprises from 0.5 to 1.5% by weight of alkali metal alkoxide and from 2.5 to 12% by weight of alkali metal formate, in each case based on the total weight of the reaction mixture ($R_M$).

10. The process according to claim 1, wherein the reaction mixture ($R_M$) is subjected to a further work-up comprising the following steps:
   (a) separation of carbon monoxide from the reaction mixture ($R_M$) in a separation apparatus to give a gas stream (G1) comprising carbon monoxide and a liquid stream (L1) comprising methyl formate, alkali metal formate, alkali metal alkoxide and methanol,
   (b) separation of the methyl formate from the liquid stream (L1) in a first distillation apparatus to give a distillate (D1) comprising methyl formate and a bottom mixture (S1) comprising alkali metal formate, alkali metal alkoxide and methanol,
   (c) division of the bottom mixture (Si) into a substream (S1a) which is recirculated to the carbonylation reactor and a substream (S1b) and
   (d) separation of the methanol from the substream (S1b) in a second distillation apparatus to give a distillate (D2) which comprises methanol and is recirculated to the first distillation apparatus and a bottom mixture (S2) comprising alkali metal formate and alkali metal alkoxide.

11. The process according to claim 1, wherein the weight ratio of substream (S1a) to substream (S1b) is greater than 50:1.

12. The process according to claim 1, wherein the molar ratio of alkali metal formate to alkali metal alkoxide in the reaction mixture ($R_M$) is greater than 2.

13. The process according to claim 1, wherein the molar ratio of alkali metal formate to alkali metal alkoxide in the reaction mixture ($R_M$) is greater than 3.

14. The process according to claim 1, wherein the molar ratio of alkali metal formate to alkali metal alkoxide in the reaction mixture ($R_M$) is greater than 5.

15. The process according to claim 1, wherein the reaction mixture ($R_M$) comprises
   from 12 to 45% by weight of methyl formate,
   from 40 to 85% by weight of methanol, from 2.5 to 15% by weight of alkali metal formate,
from 0.5 to 1.5% by weight of alkali metal alkoxide and
from 0 to 2% by weight of carbon monoxide.

16. A method for the preparation of methyl formate by carbonylation of methanol by means of carbon monoxide comprising the step of using a mixture which comprises an alkali metal formate and an alkali metal alkoxide and in which the molar ratio of alkali metal formate to alkali metal alkoxide is greater than 1 as catalyst system.

17. The method according to claim 16, wherein the molar ratio of alkali metal formate to alkali metal alkoxide is greater than 2.

* * * * *